(12) United States Patent
Randhawa

(10) Patent No.: US 12,114,857 B2
(45) Date of Patent: Oct. 15, 2024

(54) HEMOSTASIS RELOADABLE CLIP RELEASE MECHANISM

(71) Applicant: BOSTON SCIENTIFIC MEDICAL DEVICE LIMITED, Galway (IE)

(72) Inventor: Nishant Randhawa, S.A.S. Nagar (IN)

(73) Assignee: Boston Scientific Medical Device Limited, Galway (IE)

(*) Notice: Subject to any disclaimer, the term of this patent is extended or adjusted under 35 U.S.C. 154(b) by 101 days.

(21) Appl. No.: 18/052,053

(22) Filed: Nov. 2, 2022

(65) Prior Publication Data

US 2023/0293177 A1    Sep. 21, 2023

Related U.S. Application Data

(63) Continuation of application No. 16/820,347, filed on Mar. 16, 2020, now Pat. No. 11,517,316, which is a
(Continued)

(51) Int. Cl.
*A61B 17/10* (2006.01)
*A61B 17/122* (2006.01)
(Continued)

(52) U.S. Cl.
CPC ............ *A61B 17/105* (2013.01); *A61B 17/10* (2013.01); *A61B 17/1227* (2013.01);
(Continued)

(58) Field of Classification Search
CPC ............ A61B 17/1227; A61B 17/1285; A61B 17/083; A61B 17/10; A61B 17/122;
(Continued)

(56) References Cited

U.S. PATENT DOCUMENTS

2002/0045909 A1*  4/2002  Kimura ............... A61B 17/083
                                                  606/151
2003/0069592 A1    4/2003  Adams et al.
(Continued)

FOREIGN PATENT DOCUMENTS

CN        202699217        1/2013
CN        103584898        2/2014
(Continued)

OTHER PUBLICATIONS

Ge et al., "Design and analysis of a novel endoscopic successive hemostasis and closing device", Journal of Medical Biomechanics, vol. 30, No. 5, Oct. 15, 2015, 5 sheets.

*Primary Examiner* — Katherine M Shi

(74) *Attorney, Agent, or Firm* — Fay Kaplun & Marcin, LLP

(57) ABSTRACT

A system for treating tissue includes a clip assembly including clip arms movable relative to a channel of a capsule so that the clip arms are movable between a tissue receiving configuration and a tissue clipping configuration. Also, the system includes an applicator releasably coupleable to the clip assembly. The applicator includes a bushing and a control member extending therethrough. The bushing includes deflectable fingers, each of the fingers including an engaging feature at a distal end thereof to engage a corresponding engaging feature of the capsule of the clip assembly and assembled with a pusher element configured to push the fingers to a radially outward position. The pusher element includes a U-shaped portion curving into a channel of the bushing and a longitudinal portion extending distally therefrom. A cam washer is slidable over a length of the control member and positioned distally of the U-shaped portion.

20 Claims, 7 Drawing Sheets

Related U.S. Application Data continuation of application No. 15/808,569, filed on Nov. 9, 2017, now Pat. No. 10,624,642.

(60) Provisional application No. 62/425,333, filed on Nov. 22, 2016.

(51) Int. Cl.
*A61B 17/128* (2006.01)
*A61B 17/00* (2006.01)

(52) U.S. Cl.
CPC .............. *A61B 17/1285* (2013.01); *A61B 2017/00818* (2013.01); *A61B 17/1222* (2013.01)

(58) Field of Classification Search
CPC ...... A61B 17/1222; A61B 2017/12004; A61B 17/08; A61B 17/105; A61B 2017/292; A61B 2090/034
See application file for complete search history.

(56) References Cited

U.S. PATENT DOCUMENTS

| | | | |
|---|---|---|---|
| 2008/0208217 | A1 | 8/2008 | Adams |
| 2014/0135801 | A1* | 5/2014 | Menn ................ A61B 17/1285 606/142 |

FOREIGN PATENT DOCUMENTS

| | | |
|---|---|---|
| CN | 204016401 | 12/2014 |
| CN | 204133535 | 2/2015 |
| CN | 105431094 | 3/2016 |
| WO | 2008/137326 | 11/2008 |
| WO | 2016/157565 | 10/2016 |

* cited by examiner

HEMOSTASIS RELOADABLE CLIP RELEASE MECHANISM

PRIORITY CLAIM

This application is a Continuation of U.S. patent application Ser. No. 16/820,347 filed Mar. 16, 2020; which is a Continuation of U.S. patent application Ser. No. 15/808,569 filed Nov. 9, 2017, now U.S. Pat. No. 10,624,642; which claims priority to U.S. Provisional Patent Application Ser. No. 62/425,333 filed Nov. 22, 2016; the disclosure of the above application(s)/patent(s) is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Specialized endoscopic clipping devices grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present embodiments are directed to a system for treating tissue, comprising a clip assembly including a pair of clip arms, a proximal end of the clip arms connected to a yoke that is slidably received within a channel of a capsule so that the clip arms are movable between a tissue receiving configuration, in which distal ends of the clip arms are separated from one another, and a tissue clipping configuration, in which the distal ends of the clip arms are moved toward one another and an applicator releasably coupleable to the clip assembly to move the clip assembly between the tissue receiving configuration and the tissue clipping configuration. The applicator includes a bushing and a control member extending therethrough, the bushing including a plurality of deflectable fingers, distal ends of the fingers being movable radially away from a central axis of the bushing, each of the plurality of fingers including an engaging feature at a distal end thereof to engage a corresponding engaging feature of the capsule of the clip assembly and assembled with a pusher element configured to push the fingers to a radially outward position, the pusher element including a U-shaped portion curving into a channel of the bushing and a longitudinal portion extending distally therefrom, an enlarged distal end of the control member being releasably coupleable to the yoke, a cam washer being slidable over a length of the control member and positioned distally of the U-shaped portion.

In an embodiment, the engaging feature of each of the plurality of fingers may be a tab extending radially inward from the distal end of the fingers.

In an embodiment, the corresponding engaging feature of the capsule may be an increased diameter portion extending along a proximal portion of the capsule, the increased diameter portion having a larger exterior and interior diameter than a remaining portion of the capsule.

In an embodiment, the tab of the engaging feature of the bushing may engage a distal end of the increased diameter portion, when the applicator is coupled to the clip assembly.

In an embodiment, a distal-facing edge of the tab of the engaging feature may be angled with respect to a proximal end of the increased diameter portion so that, when the distal-facing edge is pushed distally against the proximal end of the increased diameter portion, each of the fingers is moved radially away from the central axis of the bushing so that the fingers are movable distally over the increased diameter portion.

In an embodiment, the cam washer may include an exterior surface that tapers from a distal end to a proximal end, the exterior surface interfacing with the U-shaped portion of the pusher element to move the longitudinal portion, and one of the plurality of fingers with which it is assembled, radially away from the central axis of the bushing to disengage the bushing from the capsule.

In an embodiment, the yoke may include a socket sized and shaped for releasably receiving the enlarged distal end of the body of the control member.

In an embodiment, the yoke may be configured to be deformed when a force exerted thereon by the enlarged distal end exceeds a predetermined threshold value.

In an embodiment, proximal ends of the clip arms may include locking tabs, proximal ends of the clip arms being biased in a radially outward position so that, when the locking tabs are received within the increased diameter portion of the capsule, the clip arms are locked in the tissue clipping configuration.

In an embodiment, the clip arms may be biased toward the tissue receiving configuration such that, when the clip arms are drawn proximally into the capsule, an interior surface of the capsule restrains the clip arms toward the tissue clipping configuration.

The present disclosure is also directed to a system for treating tissue, comprising a clip assembly including a pair of clip arms, a proximal end of the clip arms connected to a yoke that is slidably received within a channel of a capsule so that the clip arms are movable between a tissue receiving configuration, in which distal ends of the clip arms are separated from one another, and a tissue clipping configuration, in which the distal ends of the clip arms are moved toward one another, and an applicator releasably coupleable to the clip assembly to move the clip assembly between the tissue receiving configuration and the tissue clipping configuration. The applicator includes a bushing and a control member extending therethrough, the bushing including a tab extending into a channel thereof to engage a protrusion of the capsule when the capsule is received therein, the first tab including a sharpened tip for shearing off the protrusion, when a proximal force exerted on the protrusion by the tab exceeds a predetermined threshold value, to disengage the bushing from the capsule.

In one embodiment, the tab may extend from a first end connected to a wall of the capsule to a second end extending into the channel of the capsule toward a proximal end of the bushing so that the tab extends at an angle relative to a central axis along which the bushing extends.

In an embodiment, the tab may be formed by cut out of the capsule wall that is bent inward into the channel of the capsule.

In an embodiment, the yoke may include a socket sized and shaped for releasably receiving the enlarged distal end of the body of the control member and is configured to be deformed when a force exerted thereon by the enlarged distal end exceeds a predetermined threshold value.

In an embodiment, the capsule may include a guide ring extending about an exterior of the capsule distal of the protrusion, the guide ring supporting a portion of the bushing when the bushing is engaged to the capsule so that the bushing and the capsule are coaxial relative to one another.

The present disclosure is also directed to a method for treating tissue, comprising loading a first clip assembly on an applicator by coupling a control member of the applicator to a yoke at a proximal end of clip arms of the first clip assembly by pushing an enlarged distal end of the control member into a socket of the yoke and by moving fingers of a bushing of the assembly over a proximal end of a capsule of the clip assembly so that engaging features of the fingers engage a corresponding engaging feature of the capsule, inserting the loaded clip assembly to a target site within a living body via a working channel of an endoscope, moving the first clip assembly between an open configuration, in which distal ends of the clip arms are separated from one another, and a closed configuration, in which the distal ends of the clip arms are drawn toward one another, by moving the control member longitudinally relative to the capsule, locking the clip arms in the closed configuration by drawing the control member further proximally until locking tabs at a proximal end of the clip arms engage a portion of the capsule, and releasing the first clip assembly from the applicator by drawing the control member even further proximally relative to the capsule until a proximal force exerted on the yoke by the control member exceeds a predetermined threshold value so that the control member disengages from the yoke and the enlarged distal end of the control member draws a cam washer proximally against a U-shaped portion of a pusher element to move a longitudinal portion of the pusher element radially away from a central axis of the bushing to disengage a finger of the bushing, with which the pusher element is assembled, from the capsule.

BRIEF DISCLOSURE

DETAILED DESCRIPTION

Figure 1:
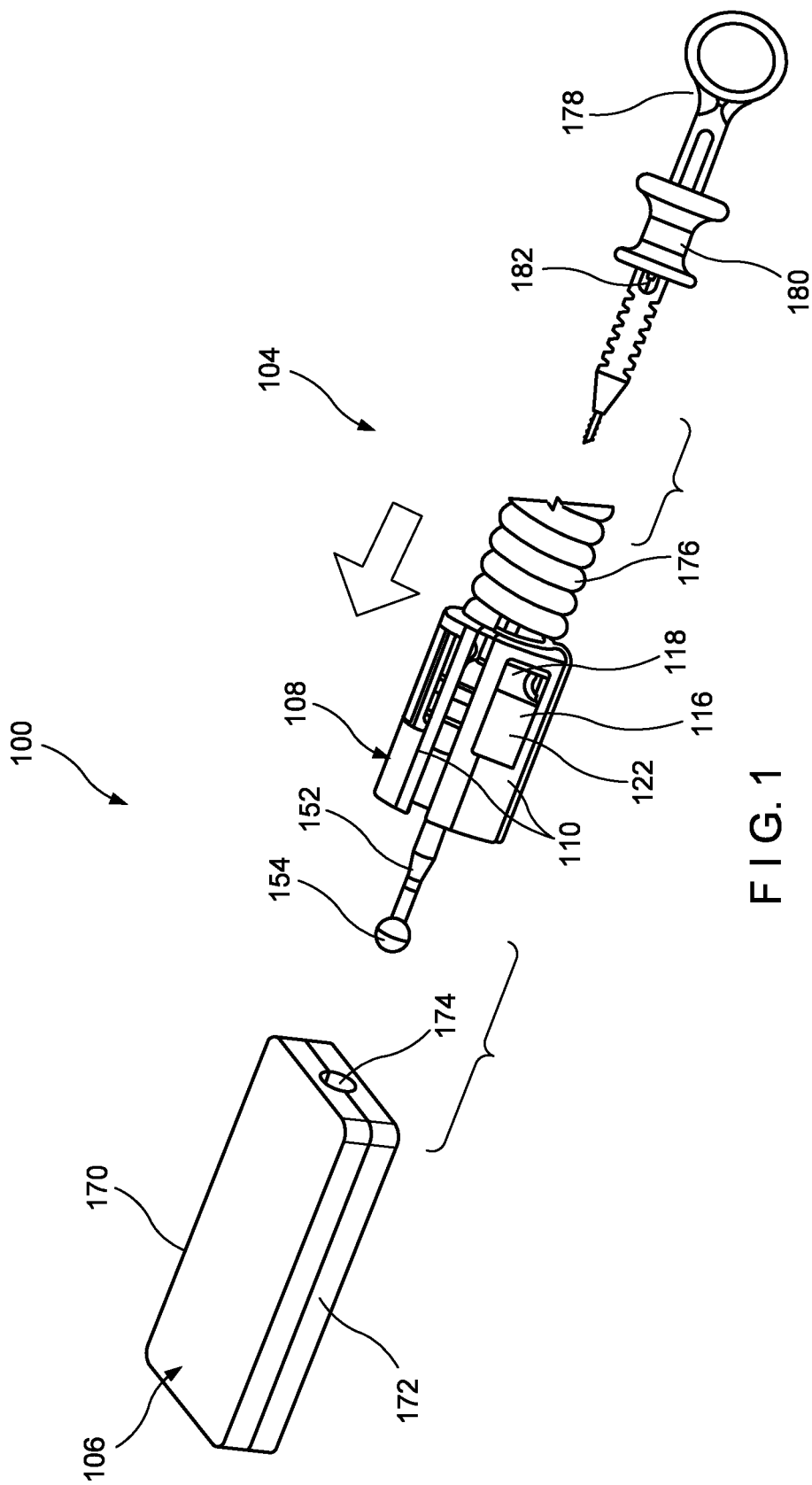
FIG. 1 shows a perspective view of a system according to an exemplary embodiment of the present disclosure.
Figure 2:
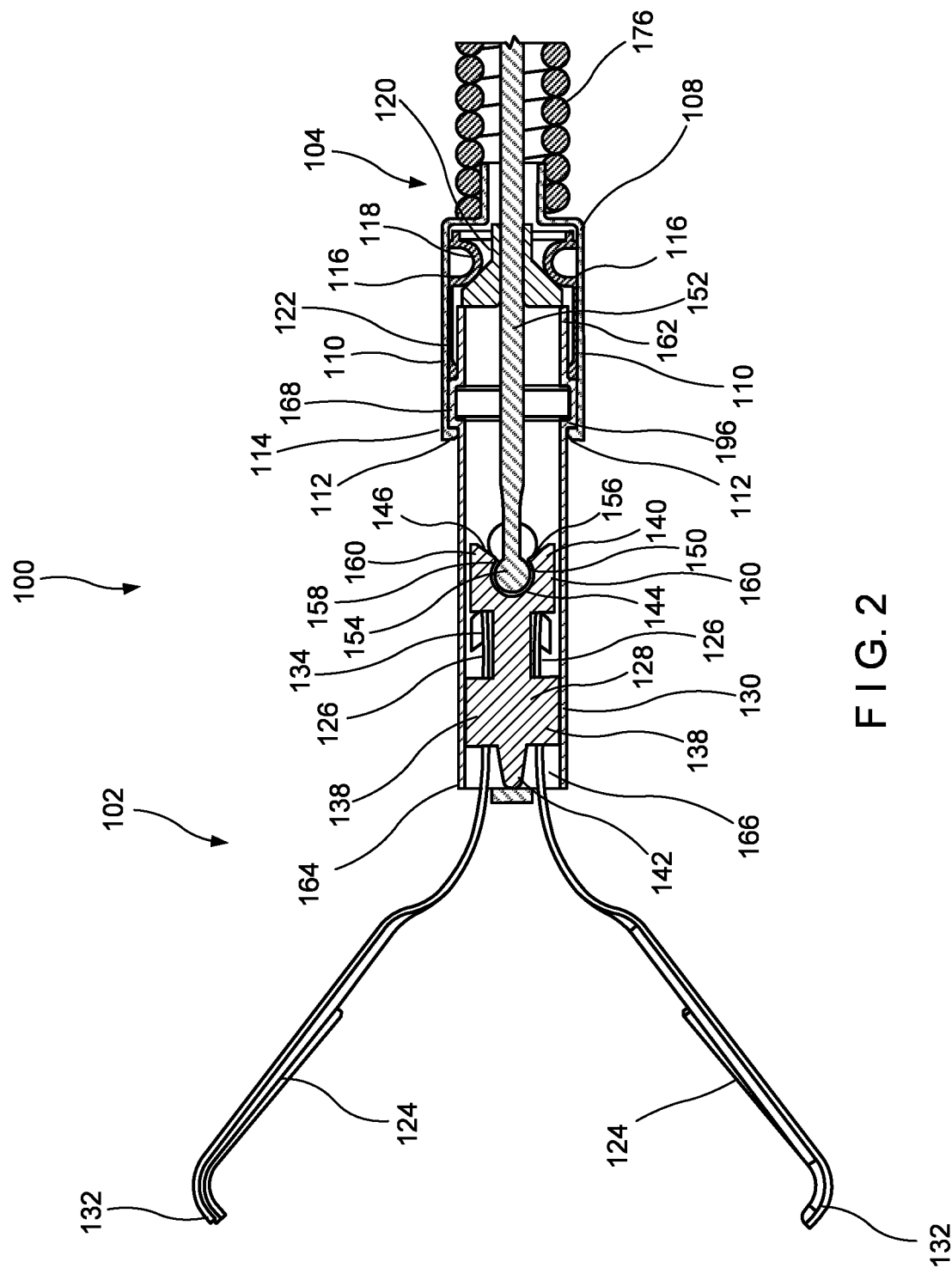
FIG. 2 shows a longitudinal cross-sectional view of a clip assembly and an applicator of the system of FIG. 1.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, the applicator assembly includes a bushing for releasably engaging the clip assembly. The bushing includes a plurality of fingers which snap over a capsule of the clip assembly. To release the clip assembly from the bushing, a cam washer may be pushed proximally against a U-shaped portion of a pusher element that is assembled with each of the plurality of fingers, so that the pusher element moves the fingers radially outward to release the clip assembly, leaving the clip assembly clipped over target tissue in the body. It should be noted that the terms "proximal" and "distal," as used herein, are intended to refer to a direction toward (proximal) and away from (distal) a user of the device.

As shown in FIGS. 1-12, a system 100 according to an exemplary embodiment of the present disclosure comprises a clip assembly 102 loadable onto a distal portion of an applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. Each clip assembly 102 according to this embodiment may be stored in a cartridge 106, which facilitates loading of the clip assembly 102 onto the applicator 104. In particular, the applicator 104 includes a bushing 108 at a distal end thereof for releasably engaging the clip assembly 102. As will be described in greater detail below, the bushing 108 includes a plurality of fingers 110 including an engaging feature 112 at a distal end 114 thereof for snapping over a portion of the clip assembly 102. Each of the plurality of fingers 110 is assembled with a pusher element 116 including a U-shaped portion 118 which, when engaged via a cam washer 120 as will be described in greater detail below, pushes a longitudinal portion 122 of the pusher element 116 against the fingers 110 to move the fingers 110 radially outward, out of engagement with the clip assembly 102.

The clip assembly 102 includes a pair of clip arms 124, proximal ends 126 of which are, in this embodiment, connected to a yoke 128 slidably received within a capsule 130. The clip arms 124 of this embodiment are biased so that distal ends 132 thereof move apart from one another into a tissue receiving configuration when not drawn into the capsule 130. When drawn into the capsule 130, an interior surface of the capsule 130 constrains the clip arms 124, holding the distal ends 132 thereof together in a tissue clipping configuration. The yoke 128 is longitudinally slidable within the capsule 130 to move the clip arms 124 between the tissue receiving configuration and the tissue clipping configuration.

Each of the clip arms 124 extends from a proximal end 126 to a distal end 132. The distal ends 132 of each of the clip arms 124 in this embodiment may project laterally inward toward the distal end 132 of the other of the clip arms 124 to facilitate gripping of target tissue therebetween. The distal ends 132 may further include other gripping features such as, for example, teeth and/or protrusions. The clip arms 124 may include features for locking the clip arms 124 within the capsule 130 in the tissue gripping configuration. For example, each of the proximal ends 126 of the clip arms 124 may include a locking tab 134 extending laterally outward therefrom. The clip arms 124 are biased so that, when the clip arms 124 are being locking in the tissue clipping configuration, the locking tab 134 of each of the clip arms 124 springs outward to lockingly engage a portion of the capsule 130. Engagement of the locking tabs 134 with the capsule 130 locks the clip assembly 102 in the tissue clipping configuration to securely grip any tissue received between the distal ends 132 of the clip arms 124 and prevents the clip arms 124 from being moved proximally out of the capsule 130.

A proximal portion of each of the clip arms 124 (e.g., distal of the locking tabs 134 at the proximal ends 126) may include an opening 136 sized and shaped to receive therein a corresponding protrusion 138 of the yoke 128 so that the clip arms 124 are engaged and aligned with the yoke 128. Thus, moving the yoke 128 relative to the capsule 130 correspondingly moves the clip arms 124 relative to the capsule 130 so that the clip arms 124 may be moved between the tissue receiving and the tissue clipping configurations via movement of the yoke 128.

The yoke 128 extends longitudinally from a proximal end 140 to a distal end 142 and includes a pair of protrusions 138 extending laterally outward from an exterior surface thereof. Each of the protrusions 138 is sized and shaped to be received within a corresponding one of the openings 136 of the clip arms 124. As described above, receipt of each of the protrusions 138 within the corresponding opening 136 of the clip arms 124 maintains the clip arms 124 in alignment relative to one another, the yoke 128 and the capsule 130. The yoke 128 further includes a longitudinal slot 144 extending from a proximal opening 146 at the proximal end 140 of the yoke 128 to a distal portion 150, which is sized and shaped to receive an enlarged end 154 of a control member 152 of the applicator 104. In one exemplary embodiment, the enlarged end 154 may be configured as a ball which is received within a correspondingly sized and shaped socket of the distal portion 150. A proximal portion 156 of the slot 144 may taper from the proximal opening 146 to a narrow opening 158 of the distal portion 150. The narrow opening 158 has a cross-sectional area (e.g., diameter) smaller than a cross-sectional area of the distal portion 150 with opposed portions 160 of the proximal portion 156 being spreadable to receive the enlarged end 154 in the distal portion 150. The opposed portions 160 are biased toward one another so that, once the enlarged end 154 is moved distally past the narrow opening 158 into the distal portion 150, the opposed portions 160 spring back to lock the enlarged end 154 within the distal portion 150, coupling the control member 152 to the yoke 128. Thus, longitudinal movement of the control member 152 relative to the capsule 130 may control movement of the clip arms 124 between the tissue receiving and the tissue clipping configurations.

Figure 10:
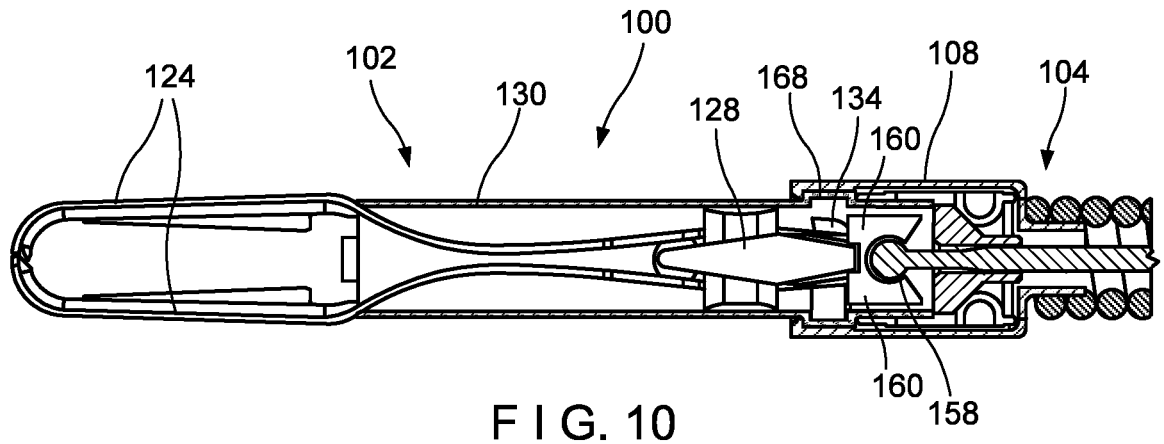
FIG. 10 shows a longitudinal cross-sectional view of the system of FIG. 1, in a locking configuration.

The capsule 130 extends longitudinally from a proximal end 162 to a distal end 164 and includes a channel 166 extending longitudinally therethrough. The channel 166 is sized and shaped to receive the yoke 128 and at least a proximal portion of the clip arms 124 therein. The capsule 130 according to this embodiment includes an increased diameter portion 168 along a proximal portion thereof, which increases both an interior diameter and an exterior diameter of the capsule 130 therealong relative to a remaining portion of the capsule 130. The increased diameter portion 168 is sized, shaped and positioned to receive the locking tabs 134. As described above, the proximal ends 126 of the clip arms 124 are biased outward so that the locking tabs 134 may ride along the interior surface of the capsule 130 until the locking tabs 134 are drawn proximally into the increased diameter portion 168, as shown in FIG. 10. When the locking tabs 134 are received within the increased diameter portion 168 of the capsule 130, the proximal ends 126 of the clip arms 124 are permitted to spring outward until the locking tabs 134 engage an interior of the increased diameter portion 168, thereby locking the clip assembly 102 in the tissue clipping configuration. The increased diameter portion 168 is positioned along the capsule 130 so that the clip arms 124 may be repeatedly moved between the tissue receiving and the clipping configurations until it is desired to lock the clip assembly 102 in the tissue clipping configuration by moving the enlarged end 154 further proximally so that the locking tabs 134 engage the increased diameter portion 168.

The increased diameter portion 168 also facilitates coupling of the clip assembly 102 to the applicator 104. Specifically, the bushing 108 of the applicator 104 may be pushed over the proximal portion of the capsule 130 until the engaging features 112 of the fingers 110 of the bushing 108 engage an exterior of the increased diameter portion 168. As will be described in further detail below, the fingers 110 are moved distally over the proximal portion of the capsule 130 until the engaging feature 112 of each of the fingers 110 is snapped over the increased diameter portion 168, thereby coupling the applicator 104 and the clip assembly 102 to one another.

Prior to being loaded on the applicator 104, the clip assembly 102 is stored in the cartridge 106, as shown in FIG. 1, which may be configured as, for example, a storage container comprising a base 170 and a lid 172. The base 170 and the lid 172 include features for coupling the base 170 and the lid 172 to one another so that the clip assembly 102 may be securely stored therein. When assembled, the base 170 and the lid 172 define a space therein sized and shaped to house the clip assembly 102. In this embodiment, the clip assembly 102 is stored in the assembled cartridge 106 in the tissue receiving configuration. The cartridge 106 includes a proximal opening 174 through which a distal portion of the applicator 104 may be inserted to be coupled to the clip assembly 102, as will be described in further detail below. The cartridge holds the clip assembly 102 in position to facilitate loading onto the applicator 104.

The applicator 104 includes the bushing 108, a flexible member 176 extending proximally therefrom, and the control member 152 extending through the bushing 108 and the flexible member 176. The applicator 104 further includes the cam washer 120 slidably mounted over the control member 152. A proximal end of the flexible member 176 is connected to a handle member 178 which includes an actuator such as, for example, a spool 180, coupled thereto. In one example, as shown in FIG. 1, the spool 180 is coupled to a proximal end 182 of the control member 152 so that, once the clip assembly 102 has been loaded onto the applicator 104, the spool 180 may be slid longitudinally over the handle member 178 to move the clip assembly 102 between the tissue receiving and clipping configurations, as described above.

Specifically, sliding the spool 180 over the handle member 178 moves the control member 152 relative to the capsule 130, which is engaged to the applicator 104. Thus, the spool 180 may also be moved relative to the handle member 178 to lock the clip assembly 102 in the tissue clipping configuration and to deploy the clip assembly in the living body.

The flexible member 176 may be formed as a coil of wire through which the control member 152 extends from the enlarged distal end 154 to the proximal end 182. As would be understood by those skilled in the art, the coil of wire preferably has sufficient flexibility to be passed through even tortuous paths of living body and, in this embodiment, is sized and shaped to permit it to be passed through a working channel of an endoscope or other insertion device. Although the flexible member 176 is shown and described as a coil of wire, it will be understood by those of skill in the art that any other suitable flexible structure may be employed so long as the flexible member 176 is capable of providing a force in compression sufficient to counter the tension to be placed on the control member 152 from the clip assembly 102. Although the applicator 104 is described as including the spool 180, the applicator 104 may include any of a variety of actuating mechanisms for moving the control member 152 to control movement of the clip arms 124.

Figure 3:
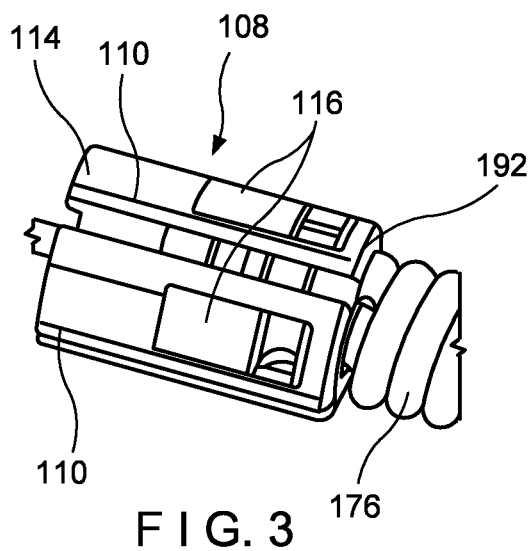
FIG. 3 shows an enlarged perspective view of a portion of the system of FIG. 1.
Figure 4:
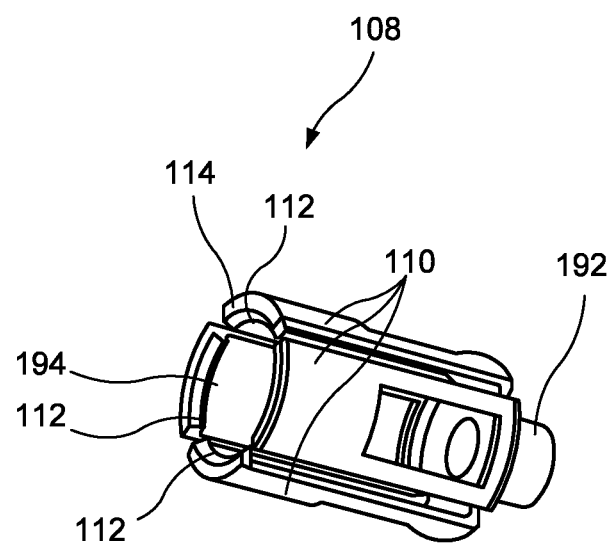
FIG. 4 shows a perspective view of a bushing of the applicator of the system of FIG. 1.
Figure 8:
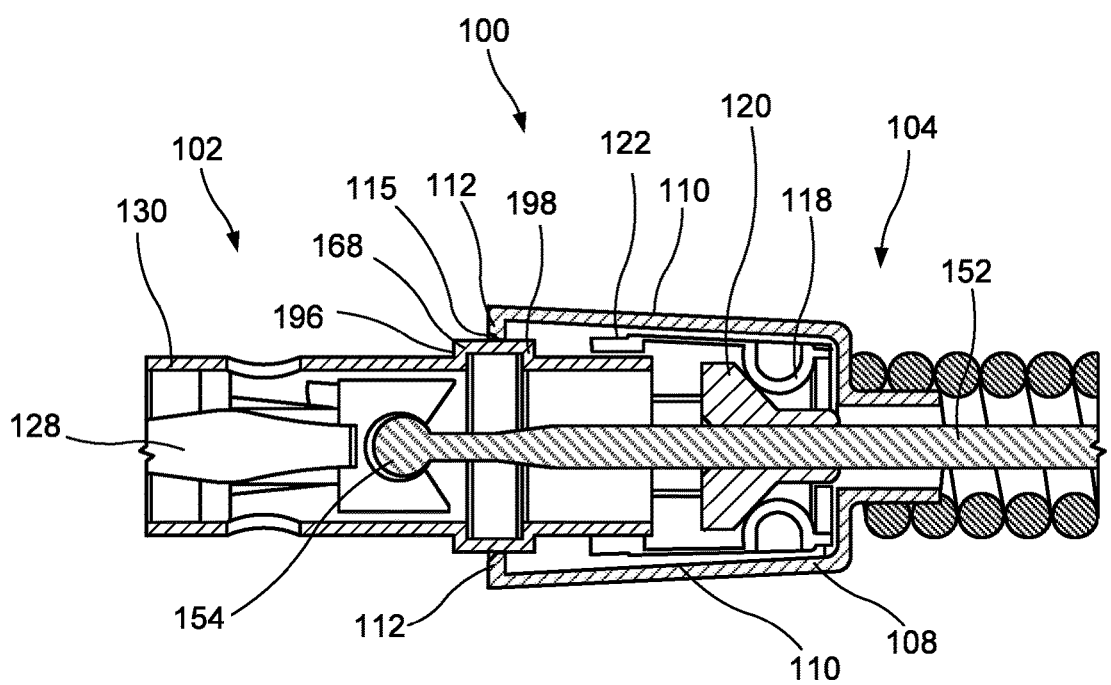
FIG. 8 shows an enlarged longitudinal cross-sectional view of a coupling between a capsule and the bushing of the system of FIG. 1.
Figure 9:
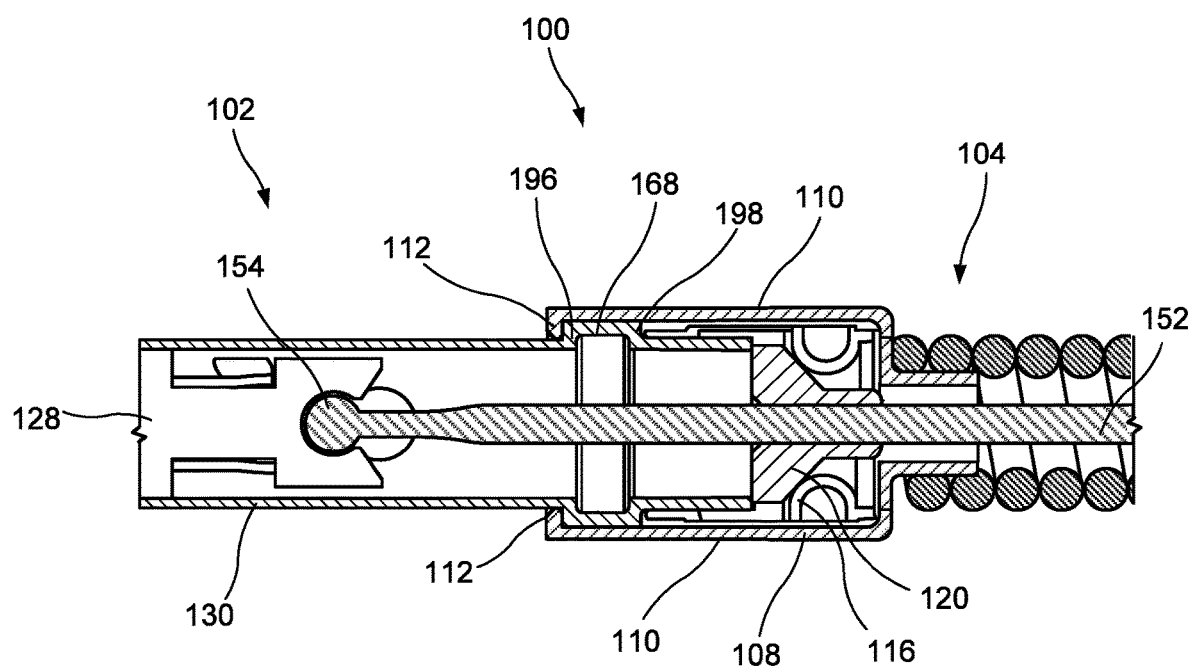
FIG. 9 shows an enlarged longitudinal cross-sectional view of the coupling and the bushing of the system of FIG. 1, in a coupled configuration.

As shown in FIGS. 3 and 4, the bushing 108 extends longitudinally along a central axis from a proximal end 192 connected to flexible member 176 to the distal end 114 and includes a channel 194 extending therethrough. As described above, the bushing 108 defines the plurality of fingers 110 moveable over the capsule 130 of the clip assembly 102 to couple the clip assembly 102 and the applicator 104 to one another. A distal end 114 of each of the fingers 110 includes the engaging feature 112 for engaging the increased diameter portion 168 of the capsule 130. The engaging features 112 of the fingers 110 may be configured as tabs extending radially inward toward the central axis of the bushing 108 to engage a distal end 196 of the increased diameter portion 168. The plurality of fingers 110 are configured to be deflectable so that distal ends 114 of the fingers 110 may be moved radially away from a central axis thereof to be moved distally over the increased diameter portion 168, as shown in FIG. 8, when pushed distally against the increased diameter portion. For example, a distal-facing edge 115 of the engaging features 112 may be angled relative to a proximal end 198 of the increased diameter portion 168 so that, when the distal-facing edge 115 is pushed distally thereagainst, each of the engaging features 112 is slid therealong to move the fingers 110 radially away from the central axis of the bushing 108. Once the engaging features 112 are moved distally past the distal end 196 of the increased diameter portion 168, as shown in FIG. 9, the fingers 110 may revert to their original position so that the tabs of the engaging feature 112 are snapped thereover to engage the distal end 196. The bushing 108 is sized and shaped so that, once the engaging feature 112 engages the increased diameter portion 168, the capsule 130 is coupled to the applicator 104 and is prevented from being moved longitudinally relative to the bushing 108. In particular, the engaging features 112 are configured such that once the engaging features 112 engage the increased diameter portion 168, a proximal force exerted thereon does not disengage the bushing 108 from the capsule 130. For example, a proximal-facing surface of the engaging feature 112 is not angled with respect to the distal end 196 of the increased diameter portion 168.

Figure 5:
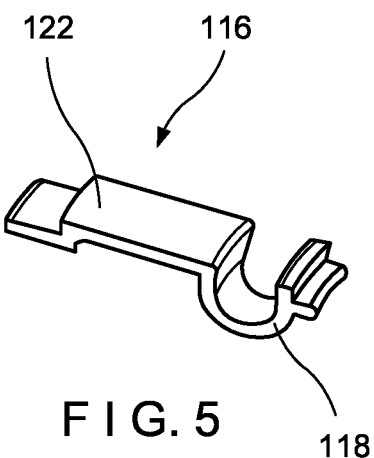
FIG. 5 shows a perspective view of a pusher element of the applicator of the system of FIG. 1.

As shown in FIGS. 3 and 5, each of the fingers 110 are assembled with the pusher element 116, which includes a U-shaped portion 118 and a longitudinal portion 122 extending distally therefrom. The U-shaped portion 118 is positioned proximate a proximal end of each of the fingers 110 so that the longitudinal portion 122 extends along a length of each of the fingers 110. The U-shaped portion 118 is curved in a substantially U-shape that extends into the channel 194 so that the cam washer 120 may interface a portion of the U-shaped portion 118. As will be described in further detail below, when the cam washer 120 interfaces with the U-shaped portion 118, the longitudinal portion 122 is moved radially away outward, away from the central axis of the bushing 108, thereby correspondingly pushing the finger 110 with which it is assembled, away from the central axis of the bushing 108 to decouple the capsule 130 from the bushing.

Figure 6:
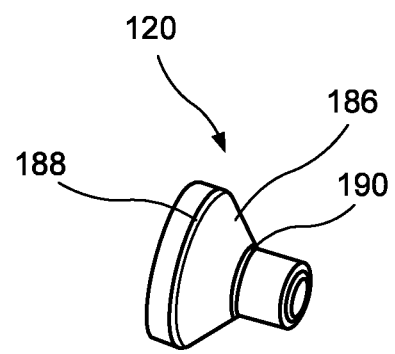
FIG. 6 shows a perspective view of a cam washer of the system of FIG. 1.
Figure 11:
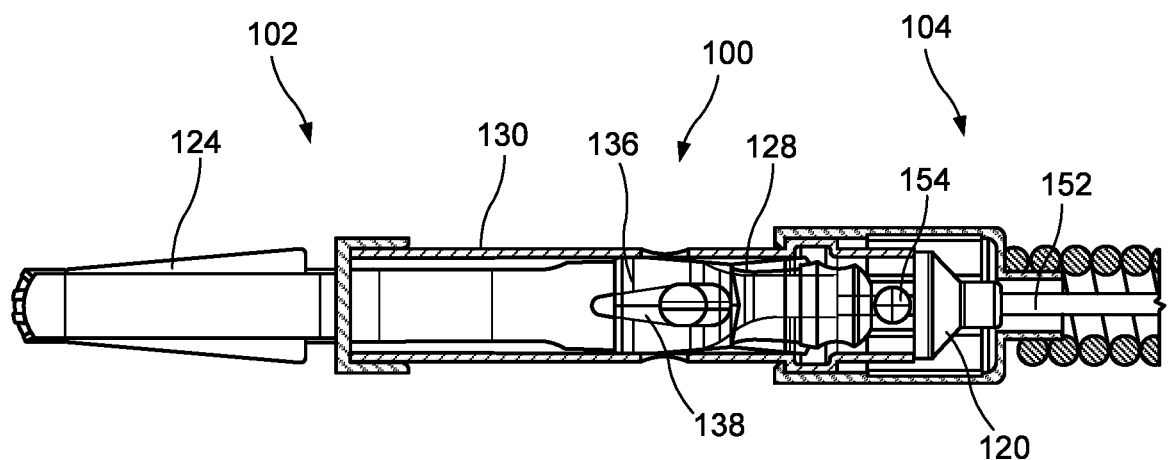
FIG. 11 shows a partially transparent longitudinal side view of the system of FIG. 1.
Figure 12:
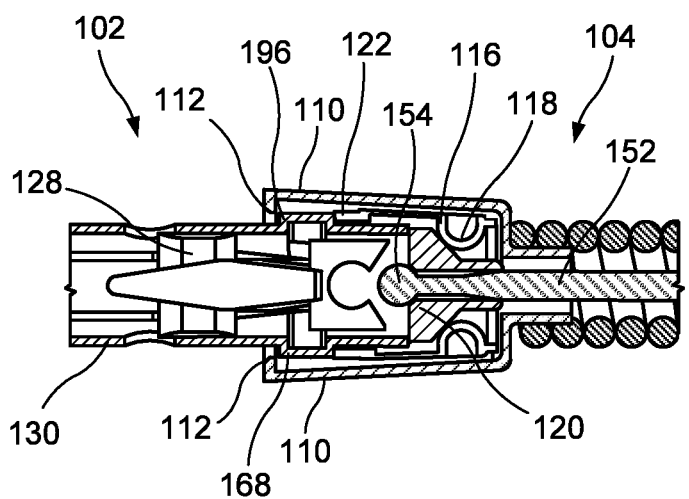
FIG. 12 shows an enlarged longitudinal side view of the bushing disengaging the capsule of the system of FIG. 1.

As described above, the control member 152 extends between the enlarged distal end 154 that is releasably coupleable to the yoke 128 and the proximal end 182 that is connected to the spool 180. A cam washer 120 is slidably mounted over a length of the control member 152 positioned within the channel 194 of the bushing 108. The cam washer 120 is positioned distally of the U-shaped portion 118 so that the cam washer 120 is slidable along the control member 152 between the enlarged distal end 154 and the U-shaped portion 118. The cam washer 120, as shown in FIG. 6, includes an exterior surface 186 which tapers from a distal end 188 toward a proximal end 190. When it is desired to deploy the clip assembly 102, the control member 152 is drawn proximally until the enlarged distal end 154 disengages the yoke 128 as shown in FIG. 11. Further proximal motion of the control member 152 causes the enlarged distal end 154 to move into contact with the cam washer 120 so that proximal motion of the control member 152 draws the cam washer 120 proximally against the U-shaped portion 118. As the cam washer 120 is pulled proximally against the U-shaped portion 118, the tapered exterior surface 186 of the cam washer 120 interfaces with the curved U-shaped portion 118. The exterior surface 186 slides against the U-shaped portion 118 causing the longitudinal portion 122 which extends therefrom to move radially away from the central axis of the bushing 108. The radial movement of the longitudinal portion 122 pushes the finger 110 with which it is assembled radially away from the central axis of the bushing 108, as shown in FIG. 12, causing the engaging feature 112 of each finger 110 to disengage from the increased diameter portion 168 of the capsule 130, releasing the clip assembly 102 from the applicator 104 and deploying the clip assembly 102 within the living body.

Figure 7:
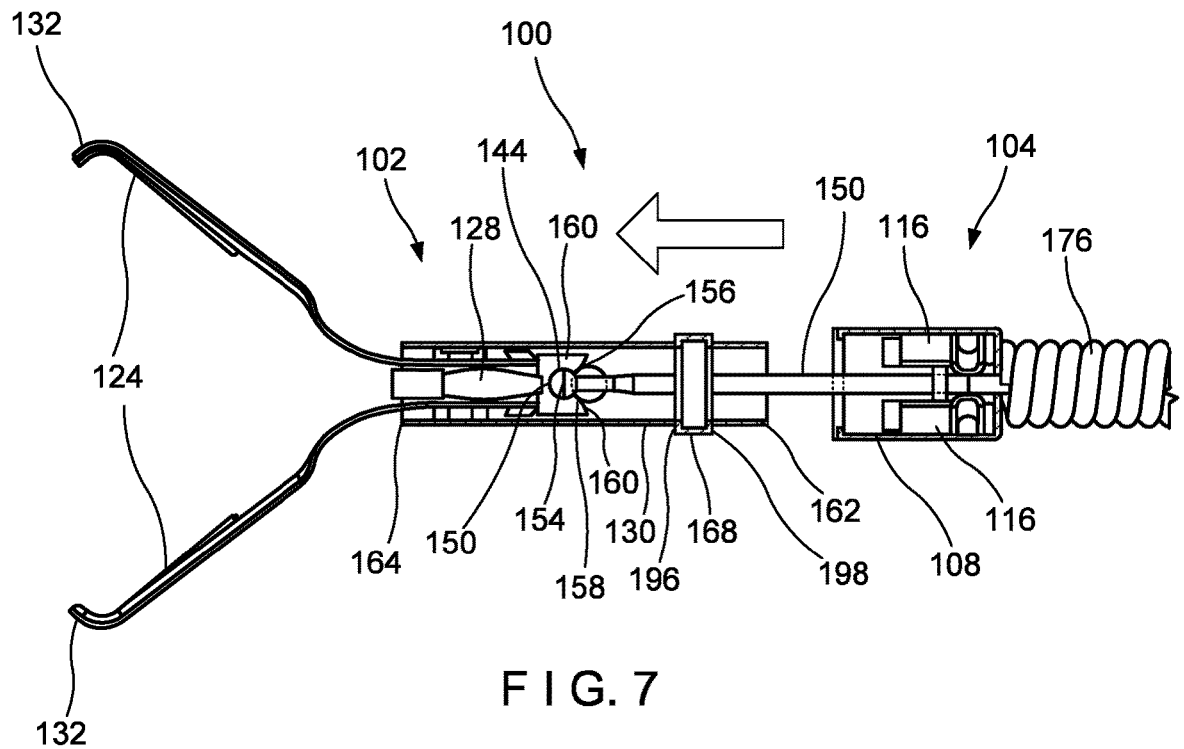
FIG. 7 shows a partially transparent longitudinal side view of the system of FIG. 1.

An exemplary method for loading the clip assembly 102 housed within the cartridge 106 to the applicator 104 comprises inserting the control member 152 and the bushing 108 of the applicator 104 through the proximal opening 174 of the cartridge 106. The enlarged end 154 of the control member 152 is moved with respect to the cartridge 106 by, for example, moving the spool 180 distally relative to the handle member 178. The enlarged end 154 is pushed distally against the yoke 128 until a distal force exerted by the enlarged end 154 against the yoke 128 exceeds a predetermined threshold value at which point opposing portions 160 of the yoke 128 move away from one another and the enlarged end 154 moves distally past the narrow opening 158 of the yoke 128 into the distal portion 150, as shown in FIG. 7. Once the enlarged end 154 has been received within the distal portion 150, the yoke 128 reverts to its original position, holding the enlarged end 154 therewithin.

Upon coupling the control member 152 to the yoke 128, the bushing 108 is moved distally over the proximal portion of the capsule 130. The engaging feature 112 of each of the fingers 110 of the bushing 108 is configured so that when the engaging feature 112 is pushed distally against the increased diameter portion 168, the fingers 110 move radially outward as the fingers 110 slide distally over the increased diameter portion 168, as shown in FIG. 8. The engaging feature 112 of each of the fingers 110 rides along an exterior surface of the increased diameter portion 168 until the engaging feature 112 moves distally past the distal end 169 of the increased diameter portion 168. As shown in FIG. 9, the fingers 110 then revert to their original position, snapping over the increased diameter portion 110 to complete the loading of the clip assembly 102 to the applicator 104. Thus, the control member 152 may be moved proximally with respect to the cartridge 106 to move the clip assembly 102 from the tissue receiving configuration to the tissue clipping configuration. Once the clip assembly 102 is in the tissue clipping configuration, the entire applicator 104 may be moved proximally relative to the cartridge 106 to draw the clip assembly 102 out of the cartridge via the proximal opening 174.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the closed configuration to facilitate its passage through the working channel. Upon reaching the site of the target tissue, the clip assembly 102 is advanced out of the distal end of the working channel and the clip arms 124 are extended distally from the capsule 130 so that the clip arms 124 spread apart from one another under their natural bias to the tissue receiving configuration. The clip arms 124 may, for example, be extended distally out of the capsule 130 by sliding the spool 180 distally relative to the handle member 178. The clip arms 124 may be advanced out of and retracted into the capsule 130 repeatedly to move the clip assembly between the open and the closed configurations until the target portion of tissue has been gripped as desired between the clip arms 124. At this point, the clip arms 124 are drawn further proximally by moving the control member 152 proximally relative to the clip assembly 102. When it is confirmed that the desired portion of tissue has been gripped between the clip arms 124 (e.g., portions of tissue on opposite sides of a bleeding wound), the control member 152 is drawn further proximally relative to the clip assembly 102 (via the spool 180) to lock the clip assembly 102 in the closed configuration. That is, the clip arms 124 are drawn further proximally into the capsule 130 until locking tabs 134 at the proximal ends 126 thereof are received within the increased diameter portion 168 of the capsule 130, as shown in FIG. 10, thereby locking the clip assembly 102 in the tissue clipping configuration.

When the clip assembly 102 is locked in the tissue clipping configuration, the clip arms 124 and the yoke 128 are fixed with respect to the capsule 130. Thus, drawing the control member 152 even further proximally relative to the clip assembly 102 exerts a force on the yoke 128. When the enlarged end 154 of the control member 152 exerts a proximal force on the yoke 128 greater than a predetermined threshold value, the yoke 128 deforms (e.g., opposed portions 160 move away from one another) to permits the enlarged end 154 to be released therefrom, as shown in FIG. 11. Once the enlarged end 154 has been released from the yoke 128, the enlarged end 154 contacts the cam washer 120, which engages the U-shaped portion 118 of the pusher element 116. As shown in FIG. 12, the cam washer 185 is slid proximally against the curved U-shaped portion, moving the pusher element 116 so that the longitudinal portion 122 is moved radially away from the central axis of the bushing 108. This movement of the longitudinal portion 122 deflects each of the fingers 110 radially away from the central axis so that the engaging feature 112 of each of the fingers 110 is moved out of engagement with the increased diameter portion 168. The control member 152 is drawn proximally until the bushing 108 is entirely disconnected from the capsule 130, releasing the clip assembly 102 from the applicator 104. The clip assembly 102 is left in the body clipped over the target tissue as the applicator 104 is withdrawn from the body. If so desired, a new clip assembly 102 is then loaded onto the applicator 104, in the same manner as described above, so that the device may then be used to clip a second portion of tissue. This process may be repeated using the same applicator 104 as many times as needed or desired.

Although the exemplary system 100 is shown and described as loading the clip assembly 102 onto the applicator 104 by mounting the bushing 108 over the capsule 130, a clip assembly may also be releasably engaged to an applicator by receiving a portion of the applicator within a proximal opening of the capsule. In addition, although the engaging features 112 are shown and described as bends along the fingers 110 of the bushing 108, other engaging features 112 are possible.

Figure 13:
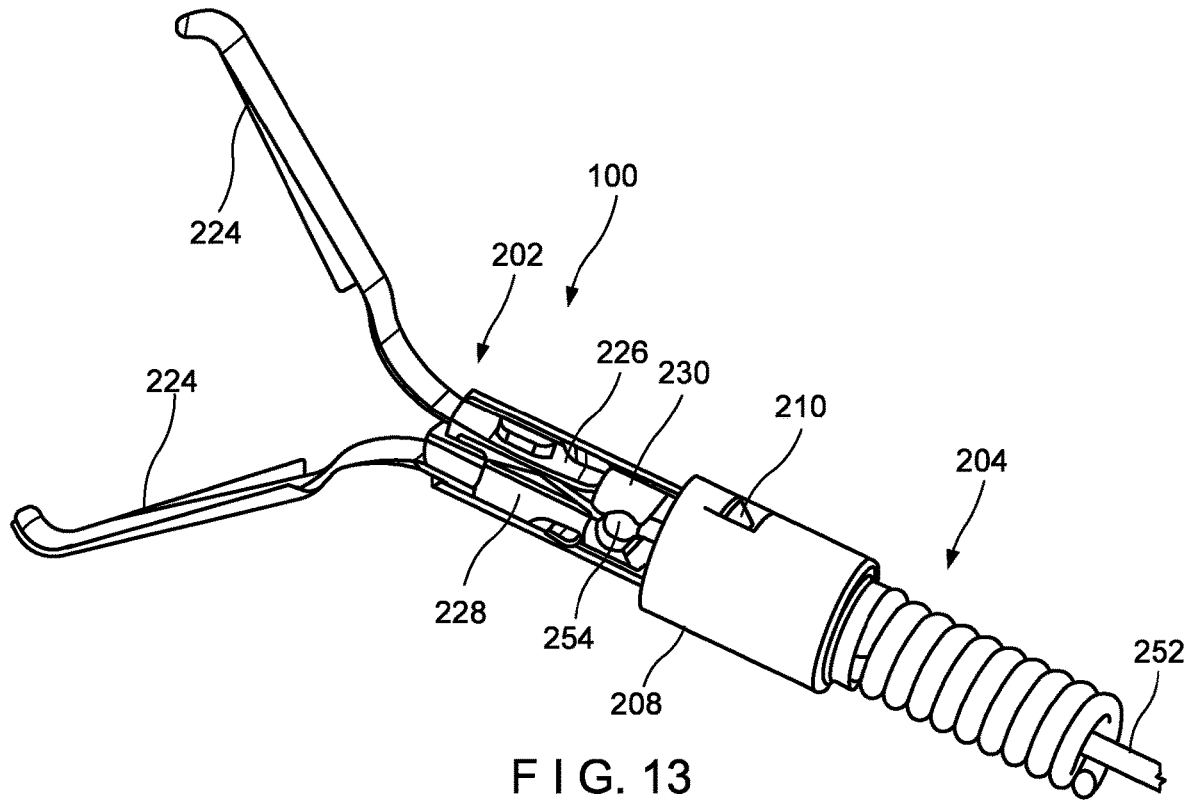
FIG. 13 shows a partially transparent perspective view of a system according to another exemplary embodiment of the present disclosure.
Figure 14:
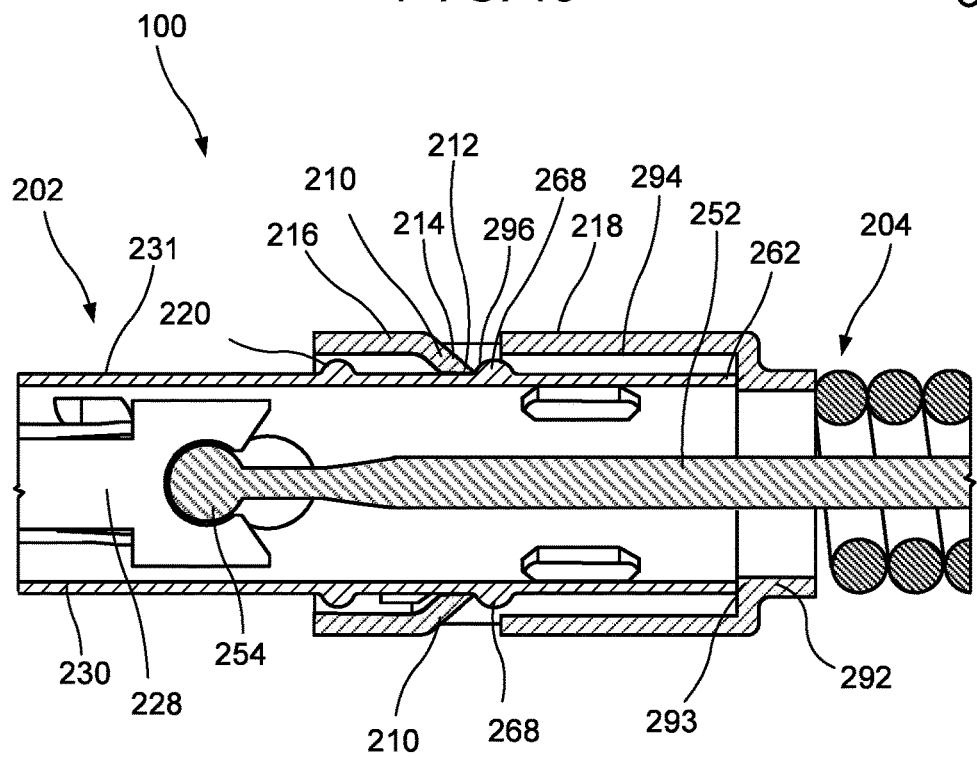
FIG. 14 shows an enlarged longitudinal cross-sectional view of a portion of the system of FIG. 13.

As shown in FIGS. 13-14, a system 200 according to another exemplary embodiment of the present disclosure may be substantially similar to the system 100, comprising a clip assembly 202 loadable onto a distal portion of an applicator 204 prior to insertion of the system 200 into a living body for the clipping of target tissue. Similarly to the applicator 104, the applicator 204 includes a bushing 208 configured to be coupled to a capsule 230 of the clip assembly 202. Rather than a plurality of fingers for engaging a portion of the capsule 230, however, the bushing 208 includes a tab 210 extending into a channel 294 thereof to engage a portion of the capsule 230, as will be described in greater detail below. The tab 210 may include a sharp tip 212 at an end 214 thereof, which shears off the portion of the capsule 230 to which the tab 210 is engaged, when it is desired to deploy the clip assembly 202 in the body.

The applicator 204 may be substantially similar to the applicator 104 described above with respect to the system 100. A distal portion of the applicator 204 includes the bushing 208 with a control member 252 extending through the channel 294 thereof. As described above, however, the bushing 208 includes the tab 210 extending into the channel 294 for engaging the capsule 230. The tab 210 may extend from a first end 216 connected to a wall 218 of the bushing 208 to a second, free end 214 which extends into the channel 294 toward a proximal end 292 of the bushing 208 so that the tab 210 extends transverse to a central axis of the bushing 208. In one embodiment, the tab 210 may be configured as a cut out through the wall 218 of the bushing 208, which is bent inward into the channel 294. The second end 214 includes a sharpened tip 212 for shearing off a portion of the capsule 230 to which the tab 210 is engaged, when it is desired to deploy the clip assembly 202 from the applicator 204.

The clip assembly 202 may be substantially similar to the clip assembly 102 described above with respect to the system 100, including clip arms 224, proximal ends 226 of which are connected to a yoke 228 slidably received within the capsule 230 to move the clip assembly 202 between a tissue receiving configuration and a tissue clipping configuration. Similarly to the clip assembly 102, the yoke 228 is configured to releasably engage an enlarged distal end 254 of the control member 252 of the applicator 204. The clip assembly 202 may be moved between the tissue receiving and the tissue clipping configurations via movement of the control member 252 in a manner substantially similarly to the clip assembly 102. When a desired target tissue has been gripped between the clip arms 224, the clip arms 224 may be locked in the tissue clipping configuration, in a manner similar to the clip assembly 102.

The capsule 230 is substantially similar to the capsule 130 of the system 100. Rather than an increased diameter portion for engaging the bushing 208 of the applicator 204, however, the capsule 230 includes a protrusion 268 extending outward from an exterior surface 231 of the capsule 230 to engage the bushing 208. Distal of the protrusion 268, the capsule 230 may further include a guide ring 220 extending about the exterior surface 231 thereof to provide support to the bushing 208 mounted over the capsule 230. In other words, the guide ring 220 maintains an alignment of the bushing 208 relative to the capsule 230 so that the bushing 208 and the capsule 230 may be coaxially aligned.

Although the exemplary embodiment describes a single tab 210 and protrusion 268, the bushing 208 and the capsule 230 may include more than one tab 210 and protrusion 268, respectively. In one example, as shown in FIG. 14, the bushing 208 may include two tabs 210 diametrically opposed from one another to engage diametrically opposed protrusions 268 of the of the capsule 230. The bushing 208 and the capsule 230, however, may include any number of corresponding tabs 210 and protrusions 268, respectively. These protrusions 268, if connected across separated ends, may form a substantially ring-like configuration.

The clip assembly 202 is loaded to the applicator 204 in a manner substantially similar to the system 100, coupling the enlarged distal end 254 of the control member 252 of the applicator to the yoke 228 of the clip assembly 202 and the bushing 208 to the capsule 230. The bushing 208, however, is coupled to the capsule 230 by moving the bushing 208 distally over the capsule 230 until the tab 210 is snapped over the protrusion 268 of the capsule 230 and/or a proximal end 262 of the capsule 230 abuts an interior shoulder 293 of the bushing 208. In other words, the second end 214 of the tab 210 engages a distal end 296 of the protrusion 268 and the shoulder 293 prevents further distal movement of the bushing 208 relative to the capsule 230. Once the clip assembly 202 is loaded to the applicator 204, the clip assembly 202 may be inserted into the body to clip target tissue.

The clip assembly 202 may be moved between the tissue receiving and the tissue clipping configurations until the desired target tissue is clipped via the clip arms 224. When the desired tissue has been clipped, the clip assembly 202 may be locked in the tissue clipping configuration, substantially as described above with respect to the system 100. Once the clip assembly 202 is locked in the tissue clipping configuration, the clip assembly 202 may be deployed by drawing the control member 252 proximally relative to the capsule 230 until the enlarged distal end 254 disengages the yoke 228. The bushing 208 is disengaged from the capsule 230 by drawing the bushing 208 proximally relative thereto until the sharpened tip 212 of the tab 210 shears through the protrusion 268. The entire applicator 204, including the control member 252 and the bushing 208 may then be removed from the body, leaving the clip assembly 202 clipped over the target tissue. As described above with respect to the system 100, if so desired, the applicator 204 may be loaded with a new clip assembly 202 to clip additional tissue within the body.

It will be apparent to those skilled in the art that various modifications may be made in the present disclosure, without departing from the scope of the disclosure.

What is claimed is:

1. A system for treating tissue, comprising:
a clip assembly including a pair of clip arms, a proximal end of the clip arms connected to a yoke that is slidably received within a channel of a capsule so that the clip arms are movable between a tissue receiving configuration, in which distal ends of the clip arms are separated from one another, and a tissue clipping configuration, in which the distal ends of the clip arms are moved toward one another; and
an applicator releasably couplable to the clip assembly to move the clip assembly between the tissue receiving configuration and the tissue clipping configuration, the applicator including a bushing and a control member extending therethrough, the bushing including a tab extending into a channel thereof to engage a protrusion of the capsule when the capsule is received therein, the tab including a sharpened tip for shearing off the protrusion, when a proximal force exerted on the protrusion by the tab exceeds a predetermined threshold value the bushing is configured to disengage from the capsule.

2. The system of claim 1, wherein the tab extends from a first end connected to a wall of the capsule to a second end extending into the channel of the capsule toward a proximal end of the bushing so that the tab extends at an angle relative to a central axis along which the bushing extends.

3. The system of claim 2, wherein the tab is formed of a cut out through the wall of the capsule that is bent inward into the channel of the capsule.

4. The system of claim 1, wherein the yoke includes a socket sized and shaped for releasably receiving an enlarged distal end of a body of the control member and is configured to be deformed when a force exerted thereon by the enlarged distal end exceeds a predetermined threshold value.

5. The system of claim 1, wherein the capsule includes a guide projecting outward and extending about a portion of an exterior of the capsule to support a portion of the bushing when the bushing is engaged to the capsule.

6. The system of claim 5, wherein the guide is a guide ring extending circumferentially about a proximal portion of the capsule distal of the protrusion and aligning the bushing and the capsule coaxially relative to one another.

7. The system of claim 1, wherein the proximal ends of the clip arms include locking tabs, the proximal ends of the clip arms being biased in a radially outward position so that, when the locking tabs are received within a portion of the capsule, the clip arms are locked in the tissue clipping configuration.

8. The system of claim 1, wherein the clip arms are biased toward the tissue receiving configuration such that, when the clip arms are drawn proximally into the capsule, an interior surface of the capsule restrains the clip arms toward the tissue clipping configuration.

9. The system of claim 1, wherein when the sharpened tip engages the protrusion, a proximal end of the capsule abuts an interior shoulder of the bushing to prevent distal movement of the bushing relative to the capsule.

10. A system for treating tissue, comprising:
a clip assembly including a pair of clip arms, a proximal end of the clip arms connected to a yoke that is slidably received within a channel of a capsule so that the clip arms are movable between a tissue receiving configuration, in which distal ends of the clip arms are separated from one another, and a tissue clipping configuration, in which the distal ends of the clip arms are moved toward one another; and an applicator releasably couplable to the clip assembly to move the clip assembly between the tissue receiving configuration and the tissue clipping configuration, the applicator including a bushing and a control member extending therethrough, the bushing including a first tab extending into a channel thereof to engage a first protrusion of the capsule when the capsule is received therein, the first tab including a first sharpened tip for shearing off the first protrusion.

11. The system of claim 10, wherein the bushing further includes a second tab extending into the channel of the bushing to engage a second protrusion of the capsule when the capsule is received therein, the second tab including a second sharpened tip for shearing off the second protrusion.

12. The system of claim 11, wherein when a proximal force exerted on the first protrusion by the first tab exceeds a first predetermined threshold value and a proximal force exerted on the second protrusion by the second tab exceeds a second predetermined threshold value the bushing is configured to disengage from the capsule.

13. The system of claim 11, wherein each of the first and second tabs extends from a first end connected to a wall of the capsule to a second end extending into the channel of the capsule toward a proximal end of the bushing so that each of the first and second tabs extends at an angle relative to a central axis along which the bushing extends.

14. The system of claim 13, wherein each of the first and second tabs is formed of a cut out through the wall of the capsule that is bent inward into the channel of the capsule.

15. The system of claim 10, wherein the yoke includes a socket sized and shaped for releasably receiving an enlarged distal end of a body of the control member and is configured to be deformed when a force exerted thereon by the enlarged distal end exceeds a predetermined threshold value.

16. The system of claim 10, wherein the proximal ends of the clip arms include locking tabs, the proximal ends of the clip arms being biased in a radially outward position so that, when the locking tabs are received within a portion of the capsule, the clip arms are locked in the tissue clipping configuration.

17. The system of claim 10, wherein the clip arms are biased toward the tissue receiving configuration such that, when the clip arms are drawn proximally into the capsule, an interior surface of the capsule restrains the clip arms toward the tissue clipping configuration.

18. The system of claim 10, wherein when the first sharpened tip engages the first protrusion, a proximal end of the capsule abuts an interior shoulder of the bushing to prevent distal movement of the bushing relative to the capsule.

19. The system of claim 10, wherein the capsule includes a guide projecting outward and extending about a portion of an exterior of the capsule to support a portion of the bushing when the bushing is engaged to the capsule.

20. The system of claim 19, wherein the guide is a guide ring extending circumferentially about a proximal portion of the capsule distal of the first protrusion and aligning the bushing and the capsule coaxially relative to one another.

* * * * *